United States Patent [19]

Zahir et al.

[11] 4,384,129

[45] May 17, 1983

[54] PROPENYL-SUBSTITUTED PHENOLGLYCIDYL ETHERS, PROCESSES FOR PRODUCING THEM, AND THEIR USE

[75] Inventors: Sheik A. Zahir, Oberwil; Sameer H. Eldin, Birsfelden, both of Switzerland

[73] Assignee: Ciba-Geigy Corporation, Ardsley, N.Y.

[21] Appl. No.: 258,196

[22] Filed: Apr. 27, 1981

Related U.S. Application Data

[63] Continuation of Ser. No. 104,507, Dec. 17, 1979, abandoned.

[30] Foreign Application Priority Data

Dec. 29, 1978 [CH] Switzerland ............... 13280/78

[51] Int. Cl.$^3$ ........................................... C07D 303/27
[52] U.S. Cl. ..................................... 549/560; 549/556; 528/101
[58] Field of Search ................... 260/348.64; 549/560, 549/556

[56] References Cited

U.S. PATENT DOCUMENTS

| | | | |
|---|---|---|---|
| 2,658,884 | 11/1953 | D'Alelio | 525/507 |
| 2,965,607 | 12/1960 | Martin et al. | 260/348.64 |
| 2,965,608 | 12/1960 | Martin et al. | 260/348.64 |
| 3,466,325 | 9/1969 | Brandstrom et al. | 260/348.49 |
| 4,130,600 | 12/1978 | Zahir et al. | 260/830 P |

FOREIGN PATENT DOCUMENTS

1306793  9/1962  France ............... 260/348.63

OTHER PUBLICATIONS

A. R. Bader, Jour. Am. Chem. Soc., (1956), vol. 78, pp. 1709–1713.
Organic Reactions, vol. II, (1944), pp. 18–19.
D. Aelony, Jour. Applied Polymer Science, vol. IV, (11), (1960), pp. 141–150.

*Primary Examiner*—Norma S. Milestone
*Attorney, Agent, or Firm*—Harry Falber

[57] ABSTRACT

Mono- and polyvalent phenolglycidyl ethers which contain in the molecule at least one 1-propenyl group in the ortho- or para-position with respect to the glycidyl ether group, or isomeric mixtures of mono- or polyvalent phenolglycidyl ethers which are propenyl-substituted in the ortho or para-position with respect to the glycidyl ether group and mono- or polyvalent phenolglycidyl ethers which are allyl-substituted in the ortho- or para-position with respect to the glycidyl ether group, the proportion of propenyl groups in the isomeric mixture having to be at least 5 equivalent-%, relative to the sum of the equivalents of propenyl and allyl groups, are obtained by a process wherein the propenyl-substituted phenols, or isomeric mixtures of propenyl- and allyl-substituted phenols, are glycidylated with an epihalohydrin. The novel compounds can be converted, both by use of curing agents for epoxide resins and by radical polymerisation, into polymers having valuable mechanical properties.

2 Claims, No Drawings

PROPENYL-SUBSTITUTED PHENOLGLYCIDYL ETHERS, PROCESSES FOR PRODUCING THEM, AND THEIR USE

This is a continuation of application Ser. No. 104,507 filed on Dec. 17, 1979, now abandoned.

The present invention relates to propenyl-substituted glycidyl ethers of mono- and polyvalent phenols, as well as to isomeric mixtures of propenyl-substituted and allyl-substituted phenolglycidyl ethers, to processes for producing them, and to the use of these compounds or isomeric mixtures for producing polymers.

Phenolglycidyl ethers which contain, besides epoxide groups, one or more allyl groups in the molecule are known.

In the German Offenlegungsschrift No. 2,726,821, there are described for example epoxide resin mixtures based on allyl-substituted phenolglycidyl ethers, which mixtures contain both maleimides and curing agents for epoxide resins. In the "Journal of Applied Polymer Science", Volume IV, No. 11, page 144, Table 2, there are given, inter alia, the mechanical properties of allyl-substituted phenolglycidyl ethers cured with m-phenylenediamine.

It has now been found that polymers having comparatively better mechanical properties are obtained by using, in place of allyl-substituted phenolglycidyl ethers, isomeric propenyl-substituted phenolglycidyl ethers, or isomeric mixtures of propenyl- and allyl-substituted phenolglycidyl ethers.

The present invention thus relates to mono- and polyvalent phenolglycidyl ethers which contain in the molecule at least one 1-propenyl group in the ortho- or para-position with respect to the glycidyl ether group; or to isomeric mixtures of mono- or polyvalent phenolglycidyl ethers which are propenyl-substituted in the ortho- or para-position with respect to the glycidyl ether group and mono- or polyvalent phenolglycidyl ethers which are allyl-substituted in the ortho- or para-position with respect to the glycidyl ether group, the proportion of propenyl groups in the isomeric mixture having to be at least 5 equivalent-%, relative to the sum of the equivalents of propenyl and allyl groups.

The invention preferably relates to phenolglycidyl ethers of the formula I

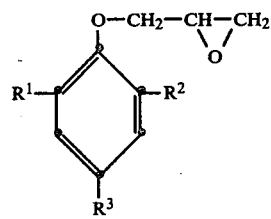

wherein $R^1$, $R^2$ and $R^3$ are each a hydrogen atom, or an allyl or propenyl group, with at least one of the substituents $R^1$ to $R^3$ being the propenyl group; of the formula II

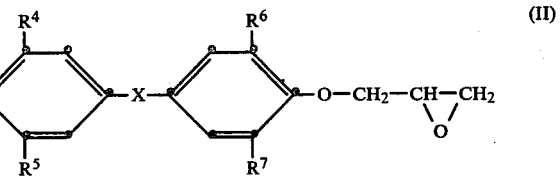

wherein $R^4$, $R^5$, $R^6$ and $R^7$ are each a hydrogen atom, or an allyl or propenyl group, with at least one of the substituents $R^4$ to $R^7$ being the propenyl group, and X is isopropylene, methylene, sulfonyl, —O— or —S—; or of the formula III

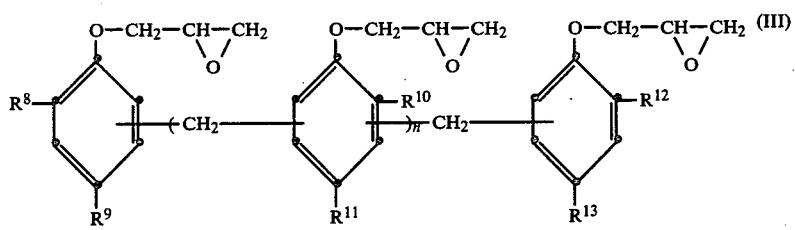

wherein $R^8$, $R^9$, $R^{10}$, $R^{11}$, $R^{12}$ and $R^{13}$ are each a hydrogen atom, alkyl having 1 to 4 carbon atoms, allyl or propenyl, with at least one of the substituents $R^8$ to $R^{13}$ being the propenyl group, and n denotes a value from zero to 10 inclusive.

Phenolglycidyl ethers of the formula II which are of particular interest are those corresponding to the formula IV

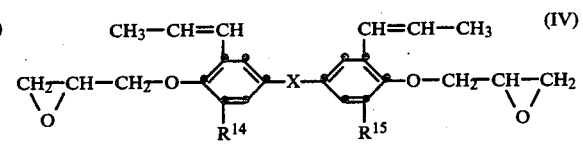

wherein $R^{14}$ and $R^{15}$ are each a hydrogen atom or a propenyl group, preferably a hydrogen atom, and X is isopropylene, methylene, sulfonyl, —O— or —S—, preferably isopropylene or methylene.

In the isomeric mixtures consisting of propenyl- and allyl-substituted mono- or polyvalent phenolglycidyl ethers, the proportion of propenyl groups is preferably at least 10 equivalent-%, particularly at least 20 equivalent-%, relative to the sum of the equivalents of propenyl and allyl groups.

In a particularly advantageous embodiment, there are used those isomeric mixtures of propenyl- and allyl-substituted mono- or polyvalent phenolglycidyl ethers wherein the proportion of propenyl groups is at least 50 equivalent-%, relative to the sum of all equivalents of propenyl and allyl groups.

The mono- or polyvalent phenolglycidyl ethers, or isomeric mixtures thereof, according to the invention, can be produced by a process wherein mono- or polyvalent phenols having in the molecule at least one 1-propenyl group in the ortho- or para-position with respect to the hydroxyl group, or isomeric mixtures of mono- or polyvalent phenols which are propenyl-substituted in the ortho- or para-position and mono- or polyvalent phenols which are allyl-substituted in the ortho- or para-position, the proportion of propenyl groups in the isomeric position being at least 5 equivalent-%, relative to the sum of the equivalents of propenyl and allyl groups, are glycidylated with an epihalohydrine.

Processes for producing glycidyl ethers of phenols by catalysed addition of epihalohydrine, especially epichlorohydrine, in the presence of tertiary amines or quaternary ammonium bases, and subsequent dehydrohalogenation of the formed halohydrine ethers by means of sodium hydroxide solution to give the phenolglycidyl ethers are known (see for example "Handbook of Epoxy Resins" by H. Lee and K. Neville, McGraw-Hill Book Co., New York, 1967, chapter 2, pages 10 to 12, and Houben-Weyl "Methoden der Organischen Chemie", Stuttgart, 1963, Vol. 14, part 2, pages 468–470). It is further known from "Journal of Applied Polymer Science", Vol. IV, pages 141 to 150 (1960) that alkenyl-substituted phenols, such as o-allylphenol and o-crotylphenol, can be glycidylated in this manner.

The propenyl-substituted phenols, or isomeric mixtures consisting of propenyl- and allyl-substituted phenols, used in the glycidylation reaction can be obtained, using the process described by A. R. Bader in the "Journal of American Chemical Society" (1956), page 1709, or using the process described in "Organic Reactions", Volume II, page 19 (1944), by alkaline isomerisation of the corresponding allyl-substituted phenols, the process comprising for example heating 2,6-diallylphenol, in the presence of at least equal amounts of potassium hydroxide solution, at above 100° C. until all the allyl groups have been isomerised to propenyl groups and the corresponding 2,6-dipropenylphenol has been formed. The result of using less than the equal amount of potassium hydroxide solution, of applying lower isomerisation temperature or of interrupting the isomerisation reaction is that isomerisation proceeds only partially, and hence the isomeric mixtures consisting of propenyl- and allyl-substituted phenols are obtained. It is naturally also possible to produce isomeric mixtures by mixing pure propenylphenols with allylphenols.

The allyl-substituted phenols are obtained, as is known, by etherification of the phenolic hydroxyl group with allyl chloride, and subsequent Claisen rearrangement. The corresponding polyallylphenols are obtained by repeating this conversion and rearrangement reaction.

As initially mentioned, the compounds and isomeric mixtures according to the invention are valuable monomers which can be processed in various ways into polymers. From the compounds according to the invention, particularly from the phenoldiglycidyl ethers, it is possible to produce, using appropriate pre-lengthening agents, such as bivalent phenols or dicarboxylic acids, by the so-called "advancement process" (see H. Batzer and S. A. Zahir in the "Journal of Applied Polymer Science", 19, pp. 585, 601 and 609 (1975) and 21, page 1843 (1977)), pre-lengthened, propenyl-substituted epoxide resins. There are thus obtained for example from n+1 mols of a propenyl-substituted phenoldiglycidyl ether and n mols of a bivalent, unsubstituted or alkenyl-substituted, phenol, where n is a number greater than 1, using the advancement process, higher-molecular epoxide resins. By the concomitant use of appropriate amounts of o-propenylphenol or o-propenylphenolglycidyl ether as chain-breaking agents, there are obtained, by the advancement process, higher-molecular resins which are free from epoxide groups, which therefore contain only alkenyl groups, especially propenyl groups, as reactive groups.

The compounds according to the invention are valuable compounds to the extent that they contain two reactive groups which differ from one another and which can be caused to crosslink either simultaneously in one curing stage or successively in a two-stage curing operation by use of appropriate curing agents and/or curing catalysts.

In the case of single-stage curing, the curing agents and/or curing catalysts required for the reaction of the reactive groups are added simultaneously. Where anionic, particularly however cationic, curing catalysts are used, further curing agents are not necessary.

For many applications, the two-stage curing procedure is of particular interest since the products obtained by reaction of the one reactive group can, optionally after application, be aftercured. It is in this manner furthermore possible to control to a certain extent the final properties of the cured moulded materials.

It is thus for example possible on the one hand to produce from the propenyl-substituted phenolglycidyl ethers, by customary polymerisation, polymers containing glycidyl groups, which can be advantageously used as polyepoxides in particular for moulding materials or in surface protection; and on the other hand it is also possible to firstly cause to react in the novel propenyl-substituted phenolglycidyl ethers the epoxide group, and to subsequently completely cure the partially cured, optionally applied, resin by means of radiation curing, for example with the aid of ionising rays.

Suitable epoxide resin curing agents are acid, basic and catalytic curing agents. The following may be mentioned as examples of curing agents which can be used: amines or amides, such as aliphatic, cycloaliphatic or aromatic primary, secondary and tertiary amines, for example ethylene diamine, hexamethylenediamine, trimethylhexamethylenediamine, diethylenetriamine, triethylenetetramine, N,N-dimethylpropylenediamine-1,3, N,N-diethylpropylenediamine-1,3, bis-(4-amino-3-methyl-cyclohexyl)-methane, 3,5,5-trimethyl-3-(aminomethyl)-cyclohexylamine ("Isophorondiamin"), Mannich bases, such as 2,4,6-tris-(dimethylaminomethyl)-phenol; p-phenylenediamine, bis-(4-aminophenyl)-methane, bis-(4-aminophenyl)-sulfone, N-(2-aminoethyl)-piperazine; polyamides, especially those from aliphatic polyamines, such as diethylenetriamine or triethylenetetramine and di- or trimerised unsaturated fatty acids, such as dimerised linseed oil fatty acid ("VERSAMID"); dicyandiamide, aniline-formaldehyde resins; polyvalent phenols, for example resorcin, 2,2-bis-(4-hydroxyphenyl)-propane or phenol-formaldehyde resins; boron trifluoride and complexes thereof with organic compounds, such as $BF_3$-ether complexes and $BF_3$-amine complexes, for example $BF_3$-monoethylamine complex; acetoacetanilide-$BF_3$ complex; phosphoric acid, triphenylphosphite; polybasic carboxylic acids and anhydrides thereof, for example phthalic anhydride, Δ⁴-tetrahydrophthalic anhydride, hexahydrophthalic anhydride, 4-methylhexahydrophthalic anhydride, 3,6-endomethylene-Δ⁴-tetrahydrophthalic anhydride, methyl-3,6-endomethylene-Δ⁴-tetrahydrophthalic anhydride (=methylnadicanhydrid), 3,4,5,6,7,7-hexachloro-3,6-endomethylene-Δ⁴-tetrahydrophthalic anhydride, succinic acid anhydride, adipic anhydride, azelaic anhydride, sebacic anhydride, maleic anhydride, dodecenylsuccinic anhydride; or pyromelitic dianhydride, or mixtures of such anhydrides.

It is also possible to use curing accelerators in the curing process; with the use of polyamides, dicyandiamide or polycarboxylic anhydrides as curing agents, suitable accelerators are for example: tertiary amines, salts or quaternary ammonium compounds thereof, for example 2,4,6-tris-(dimethylaminomethyl)-phenol, benzyldimethylamine, 2-ethyl-4-methyl-imidazole, 4-amino-pyridine or triamylammoniumphenolate; also alkali metal alcoholates, such as sodium hexanetriolate. In the case of amine curing, the accelerators used can be for example: mono- or polyphenols, such as phenol or diomethane, salicylic acid or rhodanides.

For crosslinking the polymerisable double bonds by means of radical polymerisation, there are preferably used the customary catalysts which form radicals: mention may be made of hydrazine derivatives, for example hydrazine hydrochloride, organometalic compounds, such as tetraethyl lead, as well as in particular aliphatic azo compounds, such as α,α'-azoisobutyrodinitrile and organic peroxides or persalts, for example peracetic acid, acetyl peroxide, chloroacetyl peroxide, trichloroacetyl peroxide, benzoyl peroxide, chlorobenzoyl peroxide, benzoylacetyl peroxide, propionyl peroxide, fluorochloropropionyl peroxide, lauryl peroxide, cumene hydroperoxide, cyclohexanone hydroperoxide, tert-butyl hydroperoxide, di-tert-butyl peroxide, di-tert-amyl peroxide or p-menthane hydroperoxide; also inorganic peroxide compounds, such as sodium peroxide, alkali percarbonates, alkali persulfates or alkali perborates, and particularly hydrogen peroxide, which can advantageously replace the more expensive benzoyl peroxide.

Suitable in addition to peroxides are also C-C-splitting initiators of the dibenzyl type for hot curing of the unsaturated compounds according to the invention. Initiators of the dibenzyl type are described by H. Wolfers et al. in "Kunststoffe" (Plastics), 68 (1978), No. 9, page 533.

The amount of catalyst added is regulated in a known manner according to the desired course of reaction or the desired properties of the polymer. There is advantageously used about 0.05 to 10 percent by weight of catalyst, based on the total weight of the propenyl-substituted phenol-monomer mixture, the catalyst being added either all at once at the commencement or in portions during the course of polymerisation.

In certain cases, there can also be used cationic or anionic catalysts, by which also the epoxide group can be caused to react.

The propenyl-substituted phenolglycidyl ethers according to the invention can be cured and/or polymerised or copolymerised either on their own or in admixture with other epoxide resins, and preferably with other polymerisable monomers, whilst being moulded into shaped articles or processed into sheet materials. The compounds according to the invention have very good compatibility and miscibility with other polymerisable monomers, and, in terms of quantity, a relatively large amount of these monomers can be used without impairment of the mechanical properties of the moulded articles produced therefrom. Particularly suitable as a reactive diluent is o-propenylphenolglycidyl ether, which has a low viscosity.

There can moreover be added to the propenyl-substituted phenolglycidyl ethers according to the invention, or to curable mixtures thereof, in some phase before curing, customary modifying agents, such as extenders, fillers and reinforcing agents, pigments, dyes, organic solvents, plasticisers, levelling agents, thixotropic agents, fire-retarding substances or mould release agents.

The mixtures containing curable, propenyl-substituted phenolglycidyl ethers are used in particular in the fields of surface protection, electrical engineering and laminating processes, and in the building industry. They can be used in a formulation specially adapted to suit the special purpose of application, in the unfilled or filled condition, optionally in the form of solutions or emulsions, as coating agents, lacquers, moulding materials, sintering powders, dip resins, casting resins, injection-moulding formulations, impregnating resins, binders, adhesives, tool resins, laminating resins, sealing and filler compounds, floor-covering compounds, and binders for mineral aggregates.

Unless otherwise stated in the following Examples, parts are parts by weight.

EXAMPLE 1

(a) Production of
2,2-bis-[3-(1-propenyl)-4-hydroxyphenyl]-propane

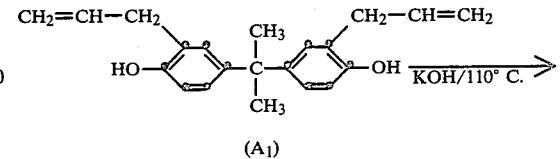

(A₁)

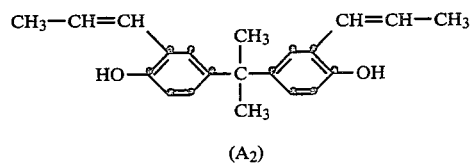

(A₂)

400 ml of methanol is slowly added, with stirring, to a mixture of 3 mols of 2,2-bis-(3-allyl-4-hydroxyphenyl)-propane (A₁) and potassium hydroxide pellets. The mixture is subsequently carefully heated to 110° C. with the distilling off of 116 ml of methanol. The reaction solution is then held, with refluxing, for a further 6 hours at 110° C. The reaction mixture is afterwards cooled, neutralised with concentrated HCl, and extracted with methylene chloride. The extract is dried, and evaporated completely to dryness. There is obtained essentially pure 2,2-bis-[3-(1-propenyl)-4-hydroxyphenyl]-propane (A₂), which at room temperature is a very highly viscous yellowish liquid. The structural formula A₂ is confirmed by microanalysis, H-NMR, MS and UV spectroscopy, as well as by means of gel-permeation chromatography.

(b) Production of 2,2-bis-[3-(1-propenyl)-4-glycidyloxyphenyl]-propane 20 mols of epichlorohydrin are added to 2 mols of 2,2-bis-[3-(1-propenyl)-4-hydroxyphenyl]-propane, and the solution is heated to 90° C. There are then added 5 g of a 1 N sodium hydroxide solution and 10 g of a 50% aqueous tetramethylammonium chloride solution, and the solution is heated, with stirring, at 90° C. for 90 minutes, in the course of which a slight exothermic reaction occurs. The solution is then cooled to 60° C., and is refluxed in a vacuum of 93 to 119 mbars, the reflux condenser being provided with a water separator (Dean-Stark Trap). 352 g of a 50% aqueous sodium hydroxide solution is slowly added, and the water is continuously removed at 60° C., by azeotropic circulatory distillation, from the reaction solution. After 2 hours, the water has been separated, and the solution is stirred at 90° C. for a further 2 hours. The solution is then cooled to 30° C., and filtered off from the salt. The filtrate is taken up in methylene chloride, and repeatedly washed with a 5% aqueous $Na_2HPO_4$ solution and water. The organic phase is separated, and dried over $Na_2SO_4$. The reaction solution is freed in a rotary evaporator from volatile constituents. There is obtained a viscous product having an epoxide content of 4.32 equivalents/kg (theory: 4.76 equivalents/kg) and a viscosity of $\eta^{40°\ C.} = 59870$ mPa.s.

H-NMR, MS and UV spectra confirm that the product obtained corresponds to the following structural formula

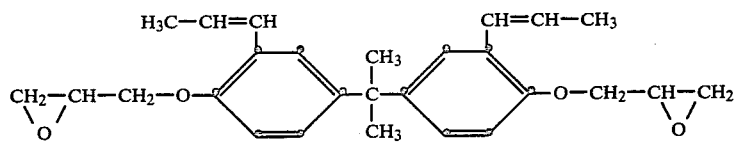

APPLICATION EXAMPLES

EXAMPLES I AND II 2,2-Bis-[3-(1-propenyl)-4-glycidyloxyphenyl]-propane having an epoxide content of 4.46 equivalents/kg (o,o'-di-(1-propenyl)-bisphenol A) and 2,2-bis-(3-allyl-4-glycidyloxyphenyl)-propane having an epoxide content of 4.53 equivalents/kg (o,o'-diallylbisphenol A) are mixed together with hexahydrophthalic anhydride and 4,4'-diaminodiphenylmethane, respectively, in the amounts given in Table 1, and the mixtures are cured. The properties of the moulded materials obtained are shown in Table 1.

TABLE 1

|  | Example I | Comparison 1 | Example II | Comparison 2 |
|---|---|---|---|---|
| o,o'-di-(1-propenyl)-bisphenol A (parts) | 100 |  | 100 |  |
| o,o'-diallylbisphenol A (parts) |  | 100 |  | 100 |
| hexahydrophthalic anhydride (parts) | 59.25 | 62.5 |  |  |
| 4,4'-diaminodiphenylmethane (parts) |  |  | 21.9 | 23.1 |
| benzyldimethylamine (parts) | 0.5 | 0.5 |  |  |
| curing conditions | 4 hours at 80° C. and 8 hours at 140° C. | | | |
| flexural strength according to Dynstat in $N/m^2 \times 10^8$ | 1.432 | 1.322 | 1.704 | 1.257 |
| glass transition temperature $T_G$ (°C.) | 118 | 97.5 | 147 | 120 |

EXAMPLES III TO VI 2,2-Bis-[3-(1-propenyl)-4-glycidyloxyphenyl]-propane having an epoxide content of 4.46 equivalents/kg (o,o'-di-(1-propenyl)-bisphenol A) and 2,2-bis-(3-allyl-4-glycidyloxyphenyl)-propane having an epoxide content of 4.53 equivalents/kg (o,o'-diallylbisphenol A) are well mixed with 2-ethyl-4-methylimidazole and maleic anhydride, respectively, in the amounts given in Table 2.

Aluminium pegs are bonded with these mixtures according to specification for the "Twist-O-Meter" (Epprecht Instruments+Controls, Bassersdorf, Switzerland), the adhesive layer being cured at the temperatures shown in Table 2. The results of the torsional shearing strength measurements are listed in Table 2.

TABLE 2

|  | Example III | Example IV | Comparison 3 | Comparison 4 | Example V | Example VI | Comparison 5 | Comparison 6 |
|---|---|---|---|---|---|---|---|---|
| o,o'-di-(1-propenyl-bisphenol A (parts) | 100 | 100 |  |  | 100 | 100 |  |  |
| o,o'-diallylbisphenol A (parts) |  |  | 100 | 100 |  |  | 100 | 100 |
| 2-ethyl-4-methylimidazole (parts) | 3 | 3 | 3 | 3 |  |  |  |  |
| tert-butylperbenzoate |  | 3 |  | 3 |  |  |  |  |
| maleic anhydride (parts) |  |  |  |  | 36.0 | 36.0 | 37.7 | 37.3 |
| benzyldimethylamine (parts) |  |  |  |  |  | 4 |  | 4 |
| curing conditions | 1 hour at 80° C., 3 hours at 150° C. and 2 hours at 200° C. | | | | 4 hours at 80° C. and 8 hours at 150° C. | | | |
| torsional shearing strength($N/m^2 \times 10^6$) | 97.2 | 96.8 | 73.0 | 70.8 | 32.6 | 88.4 | 4.0 | 71.4 |
| glass transition temperature $T_G$ (°C.) | 136 |  | 102 |  |  |  |  |  |

What is claimed is:

1. A phenolglycidyl ether of the formula IV

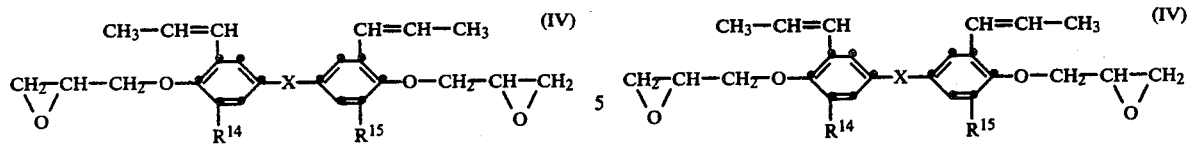 (IV)
wherein $R^{14}$ and $R^{15}$ are each a hydrogen atom and X is isopropylene, methylene, sulfonyl, —O— and —S—.
2. 2,2-Bis-[3-(1-propenyl)-4-glycidyloxyphenyl]-propane as compound of the formula IV according to claim 1.
* * * * *